US005719062A

United States Patent [19]

Kinisky

[11] Patent Number: 5,719,062

[45] Date of Patent: Feb. 17, 1998

[54] PROCESS FOR ANALYZING ANALYTES USING HF-RESISTANT ULTRASONIC NEBULIZER COMPONENTS

[75] Inventor: Thomas G. Kinisky, Shrewsbury, Mass.

[73] Assignee: Saint Gobain Industrial Ceramics Corporation, Worcester, Mass.

[21] Appl. No.: 633,196

[22] Filed: Apr. 16, 1996

Related U.S. Application Data

[62] Division of Ser. No. 469,391, Jun. 6, 1995, abandoned.

[51] Int. Cl.[6] ........ G01N 33/00

[52] U.S. Cl. ........ 436/183; 423/446

[58] Field of Search ........ 436/183; 239/102.2; 423/446; 106/14.05; 204/192.15; 505/401; 427/248.1

[56] References Cited

U.S. PATENT DOCUMENTS

| | | | |
|---|---|---|---|
| 4,109,863 | 8/1978 | Olson et al. | 239/102 |
| 4,112,297 | 9/1978 | Miyagi et al. | 250/288 |
| 4,725,344 | 2/1988 | Yocom et al. | 204/192.15 |
| 4,801,411 | 1/1989 | Wellinghoff et al. | 264/7 |
| 4,886,966 | 12/1989 | Matsunaga et al. | 250/288 |
| 4,997,678 | 3/1991 | Taylor et al. | 427/249 |
| 5,071,596 | 12/1991 | Goela et al. | 264/1.2 |
| 5,120,703 | 6/1992 | Snyder et al. | 505/401 |
| 5,157,015 | 10/1992 | Snyder et al. | 505/401 |
| 5,163,617 | 11/1992 | Clifford et al. | 239/102.2 |
| 5,254,481 | 10/1993 | Nishida | 437/4 |
| 5,258,204 | 11/1993 | Wernberg et al. | 427/255 |
| 5,266,355 | 11/1993 | Wernberg et al. | 427/248.1 |
| 5,271,957 | 12/1993 | Wernberg et al. | 427/109 |
| 5,272,308 | 12/1993 | Wiederin | 219/121.52 |
| 5,354,580 | 10/1994 | Goela et al. | 427/248.1 |
| 5,374,414 | 12/1994 | Morrish et al. | 423/446 |
| 5,393,564 | 2/1995 | Westmoreland et al. | 427/248.1 |
| 5,411,583 | 5/1995 | Bennison et al. | 106/14.05 |
| 5,451,260 | 9/1995 | Versteeg et al. | 118/725 |

OTHER PUBLICATIONS

Kirk–Othmer Encyclopedia of Chemical Technology, Third Edition, vol. 10, Ferroelectrics to Fluorine Compounds, Organic, "Fluorine Compounds, Inorganic", p. 746, 1980.

Communications of the American Ceramic Society, J. Am. Soc., 71 [2] C–72–C–74 (1988) "Liquid Corrosion and High–Temperature Oxidation Effects on Silicon Carbide/Titanium Diboride Composites", S. G. Seshadri and M. Srinivasan.

Communications of the American Ceramic Society, Sep. 1984, "Removal of Oxide Contamination from Silicon Carbide Powders", Jorulf Brynestad, Carlos E. Bamberger, Dale E. Heatherly, and J. Fred Land, pp. 184 and 185.

Chem. Technik, 44.Jg. Heft 7/8, Juli/Aug. 1992, Zur Charakterisierung der chemischen Bestandigkeit von siliciumcarbid aus dem Acheson–ProzeB.

Evaluation of an Ultrasonic Nebulizer Using Perkin–Elmer Sequential ICP Instrumentation, Robert J. Thomas and Cindy Anderau, The Perkin–Elmer Corporation, vol. 10, No. 2, Mar.–Apr. 1989.

Corrosion of silicon carbide ceramics using conventional and electrochemical methods, S. G. Cook, J. A. Little and J. E. King, pp. 183–189, 3rd International Charles Parsons Turbine Conference, Materials Engineering in Turbines and Compressors, 25–27 Apr. 1995.

Korrosion von SiC/TiC–Werkstoffen in Sauren, Corrosion of SiC/TiC materials in acids, W. Genthe, J. Kadori–al Robayie, Hausner, pp. 262–265, cfi/Ber. DKG 68 (1991) No. 6.

Jorulf Brynestad et al., "Removal of Oxide Contamination from Silicon Carbide Powders", Communications of the Anerican Ceramic Society, pp. 184 and 185 Sep. 1984.

W. Genthe et al., "Korrosion von SiC/TiC–Werkstoffen in Sauren, Corrosion of SiC/TiC materials in acids", cfi/Ber. DKG 68(1991) No. 6, pp. 262–265 1991.

Robert Thomas et al., "Evaluation of an Ultrasonic Nebulizer Using Perkin–Elmer Sequential ICP instrumentation", The Perkin–Elmer Corporation, vol. 10, No. 2, pp. 71–73 Mar.–Apr. 1989.

Cook et al., "Corrosion of silicon carbide ceramics using conventional and electrochemical methods", #rd International Charles Parsons Turbine Conference, Materials Engineering in Turbines and Compressors, pp. 183–189 Apr. 25, 1995.

*Primary Examiner*—Harold Y. Pyon
*Attorney, Agent, or Firm*—Thomas M. DiMauro

[57] ABSTRACT

A process for analyzing analytes using nebulizer component selected from the group consisting of a desolvation tube, a condenser tube, an aerosol-generator and a transducer, wherein the component has a contact surface selected from the group consisting of CVD silicon carbide, CVD diamond film and glassy carbon.

7 Claims, No Drawings

PROCESS FOR ANALYZING ANALYTES USING HF-RESISTANT ULTRASONIC NEBULIZER COMPONENTS

This is a divisional of application Ser. No. 08/469,391 filed on Jun. 6, 1995, now abandoned.

In the field of elemental analysis (e.g., Inductively Coupled Plasma Emission Spectrometry and Atomic Absorption Spectrometry), solid materials to be analyzed often need to be dissolved into a solution in order to accommodate typical analytical equipment. This is typically accomplished by digestion or dissolution in acid solutions. However, in order to insure compatibility of the acid solution with the analytical equipment, the sample solution is often diluted. This in turn dilutes the analyte concentration to the point where the detection limits of the analyzer are approached.

One way of improving the detection capabilities of these systems is to concentrate the analyte after its dissolution or decomposition. Ultrasonic nebulizers are now recognized for their ability to partially or fully desolvate sample solutions prior to their introduction into traditional analytical instruments. Simply, an ultrasonic nebulizer atomizes the sample using a piezoelectric ultrasonic transducer, concentrates the analyte by separating it from its solvent in a heated desolvation tube, condenses the solvent in a cooled condenser tube, and transports the analyte to an excitation source (i.e., flame or plasma) for analysis.

Current ultrasonic nebulizers use glass and quartz as the materials of choice for the desolvation tube, condenser tube, atomizer and transducer components in contact with (HCl) sample solutions. These silica-based nebulizers have been successfully used in many applications, including those involving analysis of trace impurities in both aqueous and organic-based acids. However, like any glass/quartz based analytical system in which trace impurities are being measured, its use is subject to restrictions. For example, the user must not select solvents which will attack the glass/quartz surface. For this reason, the analytics art has suggested that solutions having at least 10 v/o of either a strong inorganic acid or HF should not be used with glass/quartz analytic components.

When materials such as ceramics and noble metals require analysis, either strong acid solutions (hereinafter defined as those solutions having at least 10 v/o of an acid possessing a pKa of less than one) or solutions containing at least 1 v/o hydrofluoric acid ("HF") must be used as the decomposition or dissolution agent. However, it has been observed that these stronger acid solutions, and particularly HF, readily attack quartz and glass, thereby contaminating the sample with remnants from the glass/quartz components. Accordingly, the use of silica-based nebulizers has thus far been limited to dilute solutions of strong acids and solutions free of HF.

Therefore, there is a need for an adequate substitute material for selected glass/quartz components of analytical equipment which contact either strong acid solutions or solutions containing HF.

According to Kirk-Othmer's "Encyclopedia of Chemical Technology" (Vol. 10, 3rd Ed., page 746), generalizations regarding materials of construction where hydrogen fluoride and its aqueous solutions are to be handled have sometimes proved misleading, and laboratory tests give at best only general guidance. Nonetheless, this reference cites steel, carbon, lead, bronze, Monel, natural rubber, neoprene, copper, silver, PTFE and polyethylene as potential candidates that may be suitable for handling HF. It particularly cites silver as being excellent for exacting laboratory work.

Although each of steel, lead, bronze, Monel, copper and silver may be suitable for large scale storage of HF, each is also metallic. Thus, the surface of each will dissolve to some extent in the HF and/or the very strong acid solutions, thereby contaminating the sample. In addition, silver is prohibitively expensive.

Natural carbon typically contains high amounts of impurities that are soluble in strong acid solutions. In addition, it often possesses significant porosity. Accordingly, its use as a nebulizer component is not encouraged.

Although polymers such as natural rubber, neoprene, PTFE and polyethylene may possess the necessary HF and strong acid-resistance, their selection as nebulizer components raises new concerns. In particular, polymers such as these typically possess thermal diffusivities in the range of only 0.2×10 E6 m2/sec. Since a material should have a thermal diffusivity of at least about 0.4×10 E6 m2/sec to be considered suitable for use as the desolvation or condenser component or as an aerosol-generator, polymers were deemed unsuitable. Polymers likewise fail to possess the necessary stiffness required for the transducer component, which requires high stiffness in order to efficiently transmit the ultrasonic energy for atomizing the sample.

The efficiency of substituting alumina components for the quartz components has also been examined. It was believed that alumina would possess the inertness necessary to withstand HF and strong acid attack. However, significant aluminum impurities (more than 1000 ppm) were detected under typical analysis conditions.

Accordingly, there is a need to identify a material that possesses both the necessary resistance against HF and strong acid attack and either i) the necessary stiffness for its use as a transducer disk or ii) the necessary thermal conductivity for its use as a desolvation or condenser tube or as an aerosol-generator to enable its use in ultrasonic nebulizers designed to process HF-containing solutions.

SUMMARY OF THE INVENTION

In accordance with one embodiment of the present invention, there is provided a nebulizer component selected from the group consisting of a desolvation tube, a condenser tube, an aerosol generator and a transducer, wherein the component has a contact surface selected from the group consisting of CVD silicon carbide, CVD diamond film and glassy carbon.

Also in accordance with one embodiment of the present invention, there is provided a process comprising the step of:

a) contacting a liquid having at least 1 v/o of an acid selected from the group consisting of HF and an acid having a pKa of less than one with a contact surface having a composition selected from the group consisting of CVD silicon carbide and CVD diamond film.

Also in accordance with the present invention, there is provided a process comprising the steps of:

a) contacting a solution with a contact surface consisting essentially of a material selected from the group consisting of CVD silicon carbide, CVD diamond film and glassy carbon, wherein the solution comprises:
   i) an analyte, and
   ii) a solvent having at least 1 v/o of an acid selected from the group consisting of HF and an acid having a pKa of less than one, and
b) analyzing the concentration of the analyte.

DETAILED DESCRIPTION OF THE INVENTION

For the purposes of the present invention, a "contact surface" is at least some portion of a component which contacts a solvent having at least 1 v/o of an acid selected from the group consisting of HF and an acid having a pKa of less than one; "v/o" represents a volume percent; and a "strong acid solution" is a solution having at least 1 v/o of an acid having a pKa of less than one.

It has been found that CVD silicon carbide possesses the necessary properties described above to enable its advantageous use as a contact surface in the atomizer, desolvation tube, condenser tube and transducer in ultrasonic nebulizers designed to process HF-containing solutions. Experimentation has shown that a siliconized silicon carbide component which has been CVD ("chemical vapor deposition") coated with silicon carbide is essentially resistant to HF attack when exposed to a solution containing 30 v/o HF at temperatures up to 175° C. at atmospheric pressure for one hour. It was found that less than 1000 parts per million ("ppm") of contamination were generated by this contact. This discovery is unexpected in light of the literature which not only teaches how HF corrodes both siliconized and sintered SiC to produce significant silicon contamination of the HF, but also teaches that the silicon in the silicon carbide lattice behaves as free silicon when exposed to HF.

Accordingly, one skilled in the art would have expected CVD silicon carbide to be no more resistant to HF than either sintered or siliconized silicon carbide. Moreover, the SiC CVD coated-siliconized silicon carbide component has high thermal diffusivity and high stiffness, thus satisfying the thermal and mechanical requirements discussed above.

Although CVD silicon carbide appears to be the most promising contact surface for strong acid or HF-resistant analytical components, it is also contemplated that both CVD diamond film and glassy carbon may also possess the desired environmental resistance, thermal diffusivity and/or stiffness to be considered viable candidates for nebulizer component contact surfaces.

If CVD silicon carbide is selected as the contact surface, it may be produced as a monolith or deposited on a suitable substrate via any suitable conventional method. For example, deposition methods disclosed in U.S. Pat. No. 4,761,134; 4,997,678; 5,071,596; and 5,354,580, the specifications of which are incorporated herein by reference, may be used.

If CVD diamond film is selected as the contact surface, it may be produced as a monolith or deposited on a suitable substrate via any suitable conventional method. If the CVD diamond film is to be deposited on the inside of a tube (e.g., a desolvation or condenser tube), then the deposition method disclosed in U.S. Pat. No. 5,374,414, the specification of which is incorporated by reference herein, is preferred.

If glassy carbon (i.e., carbons composed of random crystallites on the order of 5 nm across) is selected as the contact surface, it may be produced by any conventional method, including pyrolysis of polymers such as cellulosics, phenol-formaldehyde resins and poly (furfuryl alcohol). Glassy carbon is available from SGL Carbon of Union, N.J.

In preferred embodiments, the desolvation and condenser tubes of the present invention have a contact surface consisting essentially of CVD silicon carbide, diamond film or glassy carbon and a base material having a thermal diffusivity of at least about 0.6×10 E6 m2/sec. Candidate base materials include graphite, CVD silicon carbide, glassy carbon, reaction-bonded silicon carbide and hot pressed silicon carbide. Preferably, the tube is either a monolithic CVD silicon carbide tube or a SiC CVD-coated silicon carbide tube. More preferably, the base material is siliconized silicon carbide, such as that disclosed in U.S. Pat. No. 3,951,587, the specification of which is incorporated herein by reference.

Similarly, the transducer of the present invention preferably has a contact surface consisting essentially of CVD silicon carbide, diamond film or glassy carbon and a base material having sufficient stiffness to efficiently transmit energy for atomizing a sample solution. Candidate base materials include graphite, CVD silicon carbide, glassy carbon, reaction-bonded silicon carbide and hot pressed silicon carbide. Preferably, the transducer is a monolithic CVD silicon carbide disk or a SiC CVD-coated silicon carbide disk. More preferably, the base material is siliconized silicon carbide, such as that disclosed in U.S. Pat. No. 3,951,587.

The components of the present invention are particularly well suited for handling any liquid having at least 1 v/o of an acid selected from the group consisting of HF and an acid having a pKa of less than one, preferably at least 10 v/o. In some processes of the present invention in which analyte concentration is determined, the contacting solution comprises at least 1 v/o of an acid selected from the group consisting of HF and an acid having a pKa of less than one, preferably at least 10 v/o, and more preferably at least 30 v/o. In these processes, the contacting liquid typically contacts the contact surface for between 1 and 10 minutes. During this contact, the temperature of the solution is at least 100° C., often between about 100° C. and 175° C. The contamination of the solution resulting from this contact typically adds less than 1000 ppm impurities to the solution.

These components may also display similar advantages in handling high base mixtures containing, for example, at least 1M sodium, potassium or ammonium hydroxide.

I claim:

1. A process for analyzing analytes comprising the steps of:

a) contacting a solution with a contact surface consisting of CVD silicon carbide, wherein the contact occurs for between 1 and 10 minutes and adds less than 1000 ppm impurities to the solution, and wherein the solution has a temperature of at least 100° C. and comprises:

i) an analyte, and ii) a solvent having at least 1 v/o HF of an acid selected from the group consisting of HF and an acid having a pKA of less than one, and b) determining the concentration of the analyte.

2. The process of claim 1 wherein the solvent contains at least 10 v/o HF.

3. The process of claim 2 wherein the solvent contains about 30 v/o HF.

4. The process of claim 1 wherein the temperature of the solution is between about 100° C. and 175° C.

5. The process of claim 4 wherein contact adds less than 1000 ppm impurities to the solution.

6. The process of claim 5 wherein the solvent comprises at least 10 v/o HF.

7. The process of claim 5 wherein the solvent comprises about 30 v/o HF.

* * * * *